(12) United States Patent
Cole et al.

(10) Patent No.: US 7,507,257 B2
(45) Date of Patent: Mar. 24, 2009

(54) INJECTABLE RESORBABLE BONE GRAFT MATERIAL, POWDER FOR FORMING SAME AND METHODS RELATING THERETO FOR TREATING BONE DEFECTS

(75) Inventors: Jantzen A. Cole, Memphis, TN (US); Michael E. Carroll, Memphis, TN (US); Jon P. Moseley, Arlington, TN (US); Kelly C. Richelsoph, Memphis, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 836 days.

(21) Appl. No.: 10/772,108

(22) Filed: Feb. 4, 2004

(65) Prior Publication Data

US 2004/0220681 A1    Nov. 4, 2004

Related U.S. Application Data

(60) Provisional application No. 60/444,690, filed on Feb. 4, 2003.

(51) Int. Cl.
*A61F 2/28* (2006.01)
(52) U.S. Cl. .................................................. 623/23.62
(58) Field of Classification Search .............. 623/23.62, 623/23.61
See application file for complete search history.

(56) References Cited

U.S. PATENT DOCUMENTS

| | | | |
|---|---|---|---|
| 1,901,051 A * | 3/1933 | Randel et al. ............... | 423/172 |
| 2,616,789 A | 11/1952 | Hoggatt et al. | |
| 3,573,947 A | 4/1971 | Kinkade et al. | |
| 3,813,312 A | 5/1974 | Kinkade et al. | |
| 4,430,760 A | 2/1984 | Smestad | |
| 4,568,536 A | 2/1986 | Kronenthal et al. | |
| 4,595,713 A | 6/1986 | St. John | |
| 4,596,574 A | 6/1986 | Urist | |
| 4,612,009 A | 9/1986 | Drobnik et al. | |
| 4,619,655 A | 10/1986 | Hanker et al. | |
| 4,650,665 A | 3/1987 | Kronenthal et al. | |
| 4,681,763 A | 7/1987 | Nathanson et al. | |
| 4,778,834 A * | 10/1988 | Murray ........................ | 523/212 |
| 4,820,306 A | 4/1989 | Gorman et al. | |
| 4,880,660 A | 11/1989 | Aasen et al. | |

(Continued)

FOREIGN PATENT DOCUMENTS

WO    WO96/39203    12/1996

(Continued)

OTHER PUBLICATIONS

Tiemann et al. Calcium sulfate hemihydrate in statoliths of deep-sea medusae. 2002. The Royal Society of Chemistry. 1266-1268.*

(Continued)

*Primary Examiner*—Thomas J Sweet
*Assistant Examiner*—Jonathan R Stroud
(74) *Attorney, Agent, or Firm*—Alston & Bird LLP

(57) ABSTRACT

An injectable resorbable bone graft material, and methods of using the same, provide increased compressive strength after injection in a bone defect. The bone graft material is made from calcium sulfate hemihydrate having a thick stubby rod-like crystalline structure and low water-carrying capacity.

36 Claims, 2 Drawing Sheets

U.S. PATENT DOCUMENTS

| | | | |
|---|---|---|---|
| 4,882,149 A | 11/1989 | Spector | |
| 4,892,734 A | 1/1990 | Leonard | |
| 4,975,526 A | 12/1990 | Kuberasampath et al. | |
| 4,994,030 A | 2/1991 | Glowczewskie et al. | |
| 5,015,449 A * | 5/1991 | Koslowski | 423/172 |
| 5,047,031 A * | 9/1991 | Constantz | 606/77 |
| 5,061,286 A | 10/1991 | Lyle | |
| 5,073,373 A | 12/1991 | O'Leary et al. | |
| 5,147,403 A | 9/1992 | Gitelis | |
| 5,162,114 A | 11/1992 | Kuberasampath et al. | |
| 5,219,897 A | 6/1993 | Murray | |
| 5,236,456 A | 8/1993 | O'Leary et al. | |
| 5,236,971 A | 8/1993 | Murray | |
| 5,264,214 A | 11/1993 | Rhee et al. | |
| 5,284,655 A | 2/1994 | Bogdansky et al. | |
| 5,290,558 A | 3/1994 | O'Leary et al. | |
| 5,298,254 A | 3/1994 | Prewett et al. | |
| 5,306,304 A | 4/1994 | Gendler | |
| 5,314,476 A | 5/1994 | Prewett et al. | |
| 5,320,844 A | 6/1994 | Liu | |
| 5,336,699 A | 8/1994 | Cooke et al. | |
| 5,356,629 A | 10/1994 | Sander et al. | |
| 5,366,507 A | 11/1994 | Sottosanti | |
| 5,385,887 A | 1/1995 | Yim et al. | |
| 5,405,390 A | 4/1995 | O'Leary et al. | |
| 5,417,975 A | 5/1995 | Lussi et al. | |
| 5,425,769 A * | 6/1995 | Snyders, Jr. | 623/23.61 |
| 5,439,684 A | 8/1995 | Prewett et al. | |
| 5,462,722 A | 10/1995 | Liu et al. | |
| 5,482,551 A | 1/1996 | Morris et al. | |
| 5,484,601 A | 1/1996 | O'Leary et al. | |
| 5,507,813 A | 4/1996 | Dowd et al. | |
| 5,510,396 A | 4/1996 | Prewett et al. | |
| 5,512,610 A | 4/1996 | Lin | |
| 5,531,791 A | 7/1996 | Wolfinbarger | |
| 5,569,308 A | 10/1996 | Sottosanti | |
| 5,573,771 A | 11/1996 | Geistich et al. | |
| 5,578,662 A | 11/1996 | Bennett et al. | |
| 5,614,206 A * | 3/1997 | Randolph et al. | 424/426 |
| 5,618,549 A | 4/1997 | Patat et al. | |
| 5,676,146 A | 10/1997 | Scarborough | |
| 5,681,873 A | 10/1997 | Norton et al. | |
| 5,697,981 A * | 12/1997 | Ison et al. | 606/63 |
| 5,700,289 A | 12/1997 | Breitbart et al. | |
| 5,707,962 A | 1/1998 | Chen et al. | |
| 5,727,945 A | 3/1998 | Dannenbaum | |
| 5,756,127 A | 5/1998 | Grisoni et al. | |
| 5,763,416 A | 6/1998 | Bonadio et al. | |
| 5,766,618 A * | 6/1998 | Laurencin et al. | 424/426 |
| 5,769,897 A | 6/1998 | Harte | |
| 5,788,976 A | 8/1998 | Bradford | |
| 5,807,567 A | 9/1998 | Randolph et al. | |
| 5,820,632 A * | 10/1998 | Constantz et al. | 423/308 |
| 5,824,087 A | 10/1998 | Aspden et al. | |
| 5,830,493 A | 11/1998 | Yokota et al. | |
| 5,861,445 A | 1/1999 | Xu et al. | |
| 5,866,155 A * | 2/1999 | Laurencin et al. | 424/425 |
| 5,899,939 A | 5/1999 | Boyce et al. | |
| 5,910,315 A | 6/1999 | Stevenson et al. | |
| 5,948,426 A | 9/1999 | Jefferies | |
| 5,948,428 A | 9/1999 | Lee et al. | |
| 5,964,805 A | 10/1999 | Stone | |
| 5,972,368 A | 10/1999 | McKay | |
| 5,981,828 A | 11/1999 | Nelson et al. | |
| 6,030,635 A | 2/2000 | Gertzman et al. | |
| 6,030,636 A | 2/2000 | Randolph et al. | |
| 6,037,519 A | 3/2000 | McKay | |
| 6,051,247 A | 4/2000 | Hench et al. | |
| 6,056,970 A | 5/2000 | Greenawalt et al. | |
| 6,071,530 A | 6/2000 | Polson et al. | |
| 6,083,522 A | 7/2000 | Chu et al. | |
| 6,118,043 A | 9/2000 | Nies et al. | |
| 6,224,635 B1 | 5/2001 | Ricci et al. | |
| 6,340,477 B1 | 1/2002 | Anderson | |
| 6,375,935 B1 * | 4/2002 | Constantz | 424/57 |
| 6,652,887 B1 | 11/2003 | Richelsoph et al. | |
| 6,753,007 B2 | 6/2004 | Haggard et al. | |
| 7,211,266 B2 | 5/2007 | Cole et al. | |
| 7,291,179 B2 | 11/2007 | Miller et al. | |
| 7,371,408 B1 | 5/2008 | Petersen et al. | |
| 7,371,409 B2 | 5/2008 | Petersen et al. | |
| 7,371,410 B2 | 5/2008 | Petersen | |
| 2002/0016636 A1 | 2/2002 | Ricci et al. | |

FOREIGN PATENT DOCUMENTS

| | | |
|---|---|---|
| WO | WO98/40113 | 9/1998 |

OTHER PUBLICATIONS

Advances in Biomaterials for Bone Regeneration. Orthopedics, vol. 26, No. 5/Supplement, May 2003.

Betz, R.R.: Limitations of Autograft and Allograft: New Synthetic Solutions. Orthopedics, 25(5 Suppl.): s561-s570 (2002).

"Bone Graft Substitutes Safe, Effective" AMA Science News Media Briefings, Dec. 6, 2001-copy unavailable.

Turner, TM, et al.: Radiographic and Histologic Assessment of Calcium Sulfate in Experimental Animal Models . . . for Local Antibiotic Delivery. J. Bone Joint Surg. 83A(Suppl.2/Pt. 1): 8-18 (2001).

Greenwald, AS, et al.: Bone-Graft Substitutes: Facts, Fictions and Applications. J. Bone Joint Surg. 83A(Suppl. 2/Pt. 2): 98-103 (2001).

Kelly, EB: New Frontiers in Bone Grafting. Orthopedic Technology Review 2(9) (2000).

Adkisson, HD, et al.: Rapid Quantitative Bioassay of Osteoinduction. J. Orthop. Res. 18(3): 503-511 (2000).

Hanker, JS: Setting of Composite Hydroxylapatite/Plaster Implants with Blood for Bone Reconstruction. Proc. 44th Ann. Meeting Electron Microscopy Society of America (1986).

Biomaterials Tutorial; www.btec.cmu.edu/tutorial/biomaterials/biomaterials.htm, undated.

* cited by examiner

INJECTABLE RESORBABLE BONE GRAFT MATERIAL, POWDER FOR FORMING SAME AND METHODS RELATING THERETO FOR TREATING BONE DEFECTS

RELATED APPLICATIONS

This application claims priority to U.S. Provision Patent Application Ser. No. 60/444,690, filed Feb. 4, 2003.

BACKGROUND OF THE INVENTION

1. Field of the Invention

The present invention pertains to bone graft materials and, more particularly, to resorbable bone graft materials optimized for strength, injection and osteoconductivity and to methods of strengthening bones using injectable, resorbable bone graft materials.

2. Brief Discussion of the Related Art

Minimally invasive surgical procedures have become very popular in the orthopedic field; and accordingly, it has become desirable to be able to inject bone graft materials in a minimally invasive manner, such as via a syringe. Since it is desirable for some bone graft materials set or cure in the body, time constraints are an issue in that the bone graft materials must maintain sufficiently low viscosity to allow injection without requiring substantial ejection force but, after injection, should, desirably, cure quickly to provide compression strength as soon as possible. Additionally, it is preferred that bone graft materials be resorbable (bioabsorbable), as opposed to bone cement which is not, and osteoconductive. The MIIG® 115 injectable bone graft material, described in U.S. Published Patent Application 2003/0185903 and marketed by Wright Medical Technology, Inc., the assignee of the present invention, is an effective injectable resorbable bone graft material made from calcium sulfate hemihydrate; however, improvements are desirable relating to working time (the time period available in which the bone graft material can be implanted in the body), injectability (the relative force required to easily inject the bone graft material through associated instrumentation using hand and/or thumb force), the set or cure time relative to compressive strength, the compressive strength achieved one hour after injection and the compressive strength achieved 24 hours after injection. Calcium sulfate hemihydrate for use as bone graft materials have, in the past, been made using hydrothermal processes where calcium sulfate dihydrate is boiled in a reaction vessel under greater than atmospheric pressure and result in a structure which requires an undesirable amount of water for hydration.

SUMMARY OF THE INVENTION

The present invention provides a high strength, injectable resorbable bone graft material for treating bone defects by implanting or injecting the injectable resorbable bone graft material therein. The term "bone defects" as used herein includes, but is not limited to, defects or voids/gaps resulting from compression fractures, benign bone cysts, diseased bone, high energy trauma, peri-articular fractures, cranial-maxillo facial fractures, osteoporotic reinforcement (ie. screw augmentation), joint arthrodesis, joint arthroplasty and periodontal reconstruction.

The injectable resorbable bone graft material of the present invention is particularly useful for minimally invasive insertion in bone defects to provide a temporary support media as well as a resorbable graft, the bone graft material being osteoconductive and replaced by bone.

The injectable bone graft material according to the present invention permits injection up to 5 minutes after mixing of calcium sulfate hemihydrate powder, with or without an accelerant, with a diluent to produce a paste, the paste achieving, within 10 minutes after injection, a compressive strength of cancellous bone, within 20 minutes after injection, achieving a compressive strength of at least the upper end of cancellous bone, and, within 24 hours after injection, achieving a compressive strength well above cancellous bone.

DESCRIPTION OF THE PREFERRED EMBODIMENT

Figure 1:
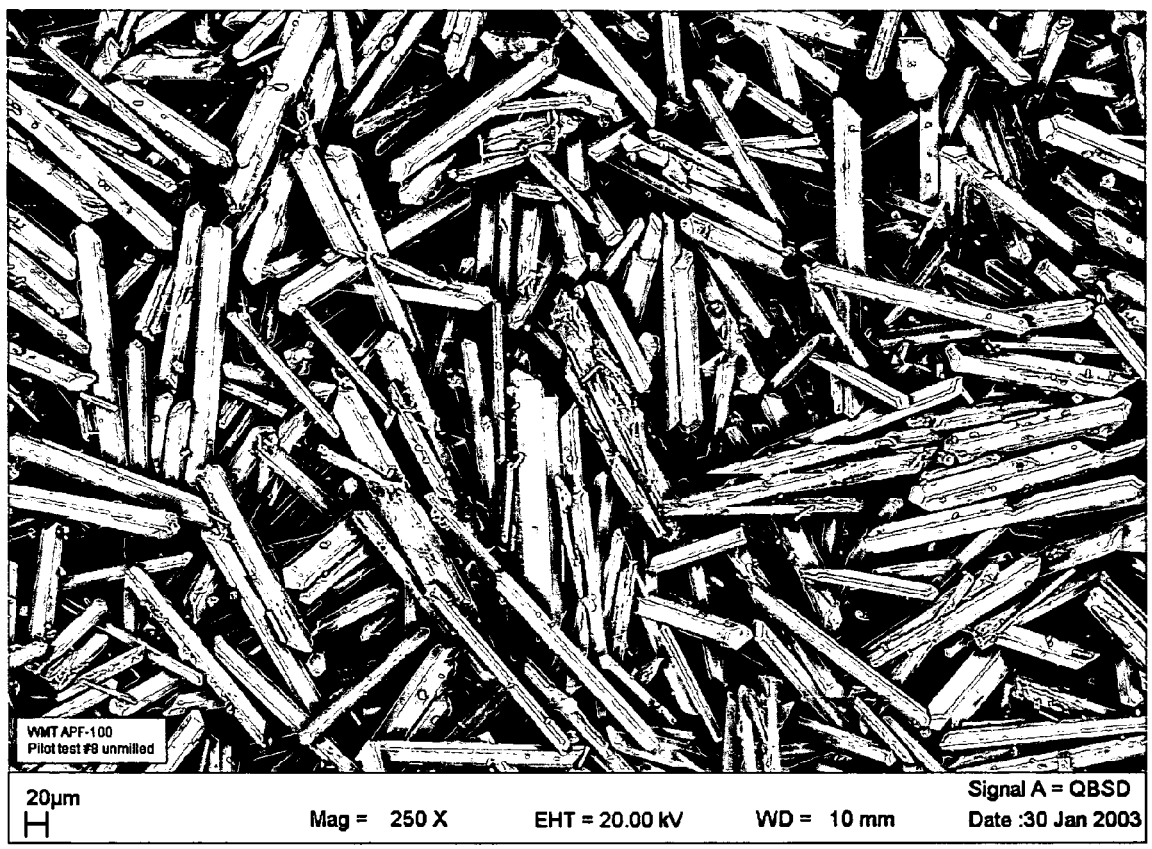
FIG. 1 is a scanning electron micrograph (SEM) depicting the crystalline structure of the calcium sulfate hemihydrate used in the present invention and in particular how it is formed of thick, stubby rod-like crystals prior to milling.
Figure 2:
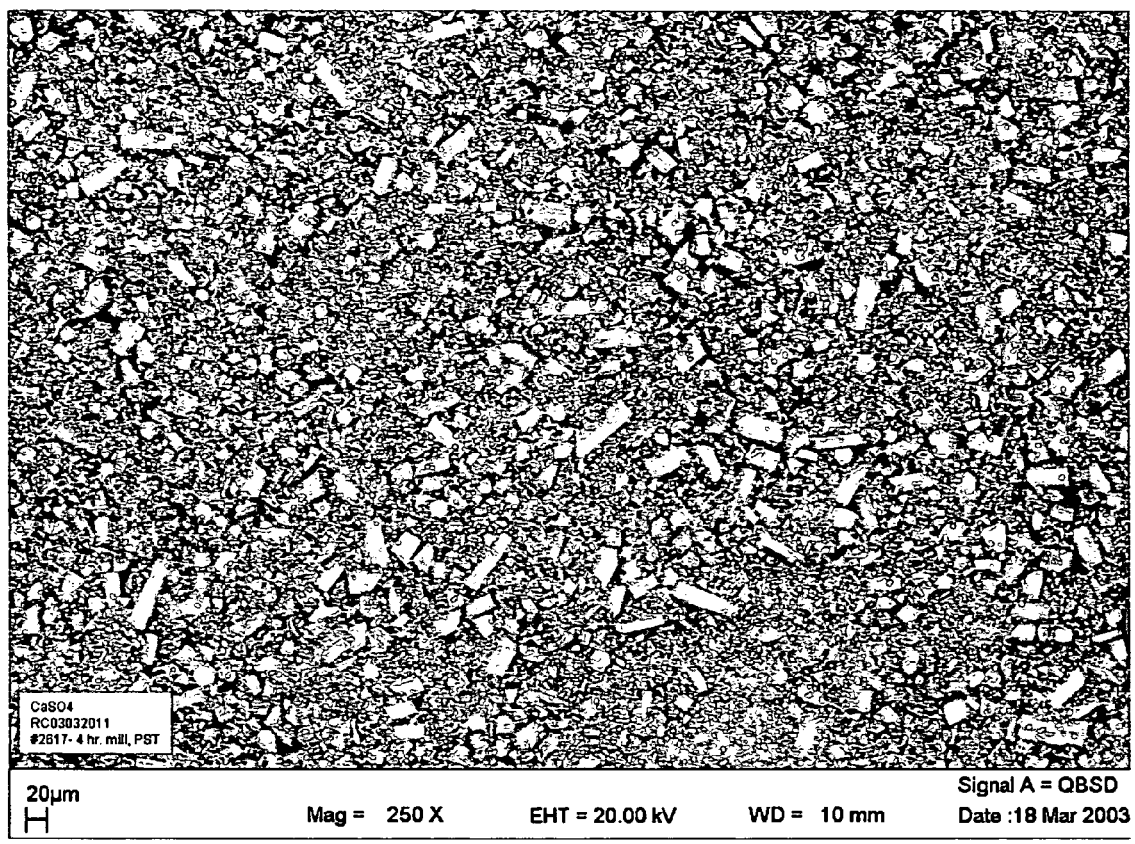
FIG. 2 is a scanning electron micrograph (SEM) depicting the crystalline structure of the calcium sulfate hemihydrate used in the present invention and in particular how it is formed of thick, stubby rod-like crystals after milling.

In accordance with the present invention, a powder is provided composed of calcium sulfate hemihydrate, in a range from 99.8% to 100% and, if the calcium sulfate hemihydrate is less that 100%, an accelerant (or accelerator), preferably calcium sulfate dihydrate, up to 0.20% may be added. The powder, calcium sulfate hemihydrate or a blend including the accelerant, is mixed with a diluent, such as sterile water, prior to insertion (or implant) in bone, the diluent to powder weight ratio range being from 0.19:1 to 0.31:1. The calcium sulfate hemihydrate is made by a known process, as disclosed in U.S. Pat. No. 2,616,789, whose contents are incorporated entirely herein by reference, where calcium sulfate dihydrate is immersed in a solution of water and an inorganic salt, such as magnesium chloride, calcium chloride, sodium chloride or other biocompatible inorganic salts selected from ammonium chloride, ammonium bromide, ammonium iodide, ammonium nitrate, ammonium sulfate, calcium bromide, calcium iodide, calcium nitrate, magnesium bromide, magnesium iodide, magnesium nitrate, sodium bromide, sodium iodide, sodium nitrate, potassium chloride, potassium bromide, potassium iodide, potassium nitrate, caesium chloride, caesium nitrate, caesium sulfate, zinc chloride, zinc bromide, zinc iodide, zinc nitrate, zinc sulfate, cupric chloride, cupric bromide, cupric nitrate, cupric sulfate alone or together. The calcium sulfate dihydrate and the solution are heated to substantially the boiling point at atmospheric pressure until a substantial portion of the calcium sulfate dihydrate is converted to calcium sulfate hemihydrate. The resulting calcium sulfate hemihydrate has a different crystalline structure than calcium sulfate hemihydrate produced by hydrothermal processes and has a lower water-carrying capacity after being milled (FIG. 2) according to conventional methods as described in the patent, but for in vivo orthopeadic applications. In particular, the crystalline structure of the calcium sulfate hemihydrate used in the present invention is formed of thick, stubby rod-like crystals, as disclosed in U.S. Pat. No. 2,616,789 (FIG. 1).

Mixing of the powder with the diluent forms a paste that is intended to be injected into bone defects, as defined above, that are not intrinsic to the stability of bony structure of the skeletal system (i.e., the extremities, spine, and pelvis) and to cure in situ. The bone defects may be surgically created osseous defects or osseous defects created from traumatic injury to the bone. The paste provides a bone void filler that resorbs and is replaced with bone during the healing process. The injectable resorbable bone graft material paste cured in situ provides an open void/gap filler that augments provisional hardware (e.g., K-Wires) to help support bone fragments during surgical procedures. The cured paste acts only as a temporary support media and is not intended to provide structural support during the healing process. In use, needles are pre-placed in defects under fluoroscopic guidance. The plunger is removed from a syringe and set aside. The powder and sterile water are placed in a bowl and mixed, preferably in a vacuum mixer. Preferably, the calcium sulfate paste is mixed in one direction for 30 seconds at a vacuum of approximately 22-25 mmHg. While mixing, the bowl should be tapped to keep the paste in the mixing zone. After mixing, a spatula is used to transfer the paste to the syringe. After the plunger is replaced, the syringe is inverted, and the plunger is advanced to remove air. The syringe is then docked to a pre-placed needle, and injection is initiated with steady thumb pressure. The total injection time should be approximately 2.5 minutes.

As noted above the calcium sulfate hemihydrate has low water-carrying capacity and is formed of thick, stubby rod-like crystals, as disclosed in U.S. Pat. No. 2,616,789. Such calcium sulfate hemihydrate has not been used, prior to the present invention, as a bone graft or substitute material. Unexpectedly, such calcium sulfate hemihydrate allows optimizing of action times and compressive strength as well as being resorbable, that is absorbable in the body within a time required to permit bone defect healing.

In accordance with the present invention, after mixing, a working time of 5 minutes or greater, depending on the amount of diluent or accelerant added, can be achieved to permit the injectable resorbable bone graft paste to be loaded into the syringe and to be injected into the bone, e.g. via the syringe and pre-placed needle. At the same time, the injectable resorbable bone graft material sets or cures quickly in the body to provide improved compressive strengths from prior art bone graft materials.

The accelerant is believed to enhance, e.g., accelerate, the conversion of calcium sulfate hemihydrate to calcium sulfate dihydrate. In particular, it is believed that particles of the accelerant act as crystallization nucleation sites for the conversion of calcium sulfate hemihydrate to calcium sulfate dihydrate. Examples of accelerants include calcium sulfate dihydrate, potassium sulfate and sodium sulfate. Other examples include ionic salts. A preferred accelerant is calcium sulfate dihydrate crystals (available from U.S. Gypsum) coated with sucrose (available from VWR Scientific Products). A process of stabilizing the dihydrate crystals by coating with sucrose is described in U.S. Pat. No. 3,573,947, hereby incorporated by reference in its entirety. Mixtures of two or more accelerants can be used.

The diluent is generally selected to provide the composition with a desired consistency and hardening time. Examples of diluent include water, e.g., sterile water, solutions containing inorganic salts, or cationic surface active agents including sodium chloride, saline, e.g., phosphate buffered saline, potassium chloride, sodium sulfate, potassium sulfate, EDTA, ammonium sulfate, ammonium acetate, and sodium acetate. Mixtures of two or more diluents can be used.

The diluent can further include, for example, bone marrow aspirate, platelet concentrate, blood, pharmaceutical additives in solution, or combinations of these materials. Examples of additives are medicaments or pesticides. Examples of medicaments are antibiotics, chemotherapeutic agents, growth factors, and analgesics. Examples of antibiotics are tetracycline hydrochloride, vancomycin, cephalosporins, and aminoglygocides such as tobramycin and gentamicin. Examples of chemotherapeutic agents are cis-platinum, ifosfamide, methotrexate, and doxorubicin hydrochloride (Adriamycin®). Examples of growth factors are transforming growth factors beta (TGF-Beta), bone morphogenic protein (BMP), basic fiberblast growth factor, platelet-derived growth factor, and other polypeptide growth factors. Examples of analgesics are anesthetics such as lidocaine hydrochloride (Xylocaine®), bipvacaine hydrochloride (Marcaine®), and non-steroidal anti-inflammatory drugs such as keterolac tromethamine (Toradol®).

As will be appreciated from the foregoing, the present invention produces an injectable resorbable bone graft material for minimally invasive implant in a bone defect utilizing a powder comprising calcium sulfate hemihydrate mixable with a diluent in a diluent to powder weight ratio from 0.19:1 to 0.31:1 to form an injectable paste and utilizing a powder formed of calcium sulfate hemihydrate and an accelerant, and a diluent mixed with the powder, the calcium sulfate hemihydrate forming, by weight, from 99.8% to 100% of the powder, the accelerant forming, by weight, from 0% to 0.2% of the powder, and the diluent to powder weight ratio being from 0.19:1 to 0.31:1. In a specific example, the accelerant is calcium sulfate dihydrate and the diluent is sterile water, the calcium sulfate hemihydrate forms 99.99% of the powder by weight, the calcium sulfate dihydrate forms 0.01% of the powder by weight and the sterile water to powder weight ratio is 0.25:1. Additionally the present invention includes treating bone defects by injecting a resorbable bone graft material in the form of a paste by mixing calcium sulfate hemihydrate having thick stubby rod-like crystals with water.

The following examples show the efficacy of the inventive materials and methods according to the invention.

EXAMPLE ONE

A 35-gram mixture of powder having 99.995% calcium sulfate hemihydrate manufactured as described above and and 0.005% calcium sulfate dihydrate is placed into a bowl with about 8.75 g of water and the two are mixed (water-to-powder ratio=0.25), preferably in a vacuum mixer. Preferably the calcium sulfate paste is mixed in one direction for 30 seconds at a vacuum of approximately 22-25 mmHg. The resulting paste is placed into a syringe and can be injected through a 6 cm long, 11-gauge needle. Following procedures similar to ASTM-F451, cylindrical samples (6 mm in diameter, 12 mm high) can be formed for compressive strength testing. The specimens are allowed to cure at atmospheric pressure (no pressure applied to curing specimens) in air at approximately 21 deg C. for 1 hour and 24 hours then subjected to compression tests. This is known as dry-testing.

EXAMPLE TWO 35-grams mixture of 99.995% calcium sulfate hemihydrate powder manufactured as described above and placed into a bowl with about 6.65 g of water and the two are mixed (water-to-powder ratio=0.19), preferably in a vacuum mixer. Preferably the calcium sulfate paste is mixed in one direction for 30 seconds at a vacuum of approximately 22-25 mmHg. The resulting paste is placed into a syringe and can be injected through a 6 cm long, 11-gauge needle. Following procedures similar to ASTM-F451, cylindrical samples (6 mm in diameter, 12 mm high) can be formed for compressive strength testing. The specimens are allowed to cure at atmospheric pressure (no pressure applied to curing specimens) in air at approximately 21 deg C. for 1 hour and 24 hours then subjected to compression tests. This is the dry-test.

EXAMPLE THREE 35-grams mixture of 99.995% calcium sulfate hemihydrate powder manufactured as described above and placed into a bowl with about 8.05 g of water and the two are mixed (water-to-powder ratio=0.23), preferably in a vacuum mixer. Preferably the calcium sulfate paste is mixed in one direction for 30 seconds at a vacuum of approximately 22-25 mmHg. The resulting paste is placed into a syringe and can be injected through a 6 cm long, 11-gauge needle. Following procedures similar to ASTM-F451, cylindrical samples (6 mm in diameter, 12 mm high) can be formed for compressive strength testing. The specimens are allowed to cure at atmospheric pressure (no pressure applied to curing specimens) in bovine serum at 37° C. for 1 hour and 24 hours then subjected to compression tests. This is known as wet-testing and the results from this mode of testing are believed to be more indicative of the type of results that would result from the actual in vivo use of the material. However, the dry-testing results are correlated to wet-testing results, in the sense that the higher the compressive strength obtained in the dry-test, the higher the compressive strength that can be expected through the wet-test.

Results

| Example | Set Time | Mean Compressive Strength (MPa) | Maximum Compressive Strength (MPa) |
| --- | --- | --- | --- |
| One (dry) | 1 hour | ≈45 | ≈50 |
| One (dry) | 24 hours | ≈88 | ≈98 |
| Two (dry) | 1 hour | ≈49 | ≈54 |
| Two (dry) | 24 hours | ≈98 | ≈106 |
| Three (wet) | 1 hour | ≈49 | ≈52 |
| Three (wet) | 24 hours | ≈56 | ≈59 |

After initial testing of similar samples using the same protocols, compressive strengths of 15 MPa (@ 1 hour) 35 MPa (@ 24 hours) were reported in U.S. Provisional Patent Application Ser. No. 60/444,690. The current test results exceed those early test results. As testing and mixing protocols improve, it is foreseen that the various compressive strengths produced by the invention will further increase. Accordingly, the disclosed examples are merely exemplary and not meant to be limiting.

What is claimed is:

1. A method for treating bone defects comprising the steps of mixing a powder comprising between about 99.8 to 100 percent by weight calcium sulfate hemihydrate, the calcium sulfate hemihydrate consisting of thick, stubby, rod-like crystals having a low water carrying capacity, with a diluent to produce an injectable resorbable bone graft material in the form of a paste; and injecting the injectable resorbable bone graft material in the bone defect, the injectable resorbable bone graft material having a compressive strength in excess of 15 MPa within one hour after said injecting step.

2. The method of claim 1, wherein said bone graft material has a compressive strength of approximately 45-49 MPa within one hour after said injecting step.

3. The method of claim 1, wherein said bone graft material has a compressive strength exceeding approximately 50 MPa within one hour after said injecting step.

4. The method of claim 1, wherein the diluent is water or a solution comprising an inorganic salt or a cationic surface active agent.

5. The method of claim 1, wherein the calcium sulfate hemihydrate is formed by immersing calcium sulfate dihydrate in a solution of water and an inorganic salt to form a mixture, and heating the mixture to substantially its boiling point at atmospheric pressure such that the calcium sulfate dihydrate is converted to calcium sulfate hemihydrate.

6. The method of claim 1, wherein the injectable resorbable bone graft material has a working time of at least 5 minutes following mixing.

7. The method of claim 1, wherein the injectable resorbable bone graft material further comprises an accelerant.

8. The method of claim 7, wherein the accelerant is selected from the group consisting of calcium sulfate dihydrate, calcium sulfate dihydrate coated with sucrose, potassium sulfate, and sodium sulfate.

9. The method of claim 1, wherein the injectable resorbable bone graft material further comprises one or more additives selected from the group consisting of bone marrow aspirate, platelet concentrate, blood, antibiotics, chemotherapeutic agents, growth factors, and analgesics.

10. The method of claim 1, wherein the diluent to powder weight ratio is 0.19:1 to 0.31:1.

11. A method for treating bone defects comprising the steps of mixing a powder comprising between about 99.8 to 100 percent by weight calcium sulfate hemihydrate, the calcium sulfate hemihydrate consisting of thick, stubby, rod-like crystals having a low water carrying capacity, with a diluent to produce an injectable resorbable bone graft material in the form of a paste; and injecting the injectable resorbable bone graft material in the bone defect, said injectable resorbable bone graft material having a compressive strength of at least 6 MPa within 20 minutes after said injecting step.

12. The method of claim 11, wherein the diluent is water or a solution comprising an inorganic salt or a cationic surface active agent.

13. The method of claim 11, wherein the calcium sulfate hemihydrate is formed by immersing calcium sulfate dihydrate in a solution of water and an inorganic salt to form a mixture, and heating the mixture to substantially its boiling point at atmospheric pressure such that the calcium sulfate dihydrate is converted to calcium sulfate hemihydrate.

14. The method of claim 11, wherein the injectable resorbable bone graft material has a working time of at least 5 minutes following mixing.

15. The method of claim 11, wherein the injectable resorbable bone graft material further comprises an accelerant.

16. The method of claim 15, wherein the accelerant is selected from the group consisting of calcium sulfate dihydrate, calcium sulfate dihydrate coated with sucrose, potassium sulfate, and sodium sulfate.

17. The method of claim 11, wherein the injectable resorbable bone graft material further comprises one or more additives selected from the group consisting of bone marrow aspirate, platelet concentrate, blood, antibiotics, chemotherapeutic agents, growth factors, and analgesics.

18. The method of claim 11, wherein the diluent to powder weight ratio is 0.19:1 to 0.31:1.

19. A method for treating bone defects comprising the steps of mixing a powder comprising between about 99.8 to 100 percent by weight calcium sulfate hemihydrate, the calcium sulfate hemihydrate consisting of thick, stubby, rod-like crystals having a low water carrying capacity, with a diluent to produce an injectable resorbable bone graft material in the form of a paste; and injecting the injectable resorbable bone graft material in the bone defect, said injectable resorbable bone graft material having a compressive strength of at least 35 MPa within 24 hours after said injecting step.

20. The method of claim 19, wherein said bone graft material has a compressive strength of approximately 56 MPa within 24 hours after said injecting step.

21. The method of claim 19, wherein the diluent is water or a solution comprising an inorganic salt or a cationic surface active agent.

22. The method of claim 19, wherein the calcium sulfate hemihydrate is formed by immersing calcium sulfate dihydrate in a solution of water and an inorganic salt to form a mixture, and heating the mixture to substantially its boiling point at atmospheric pressure such that the calcium sulfate dihydrate is converted to calcium sulfate hemihydrate.

23. The method of claim 19, wherein the injectable resorbable bone graft material has a working time of at least 5 minutes following mixing.

24. The method of claim 19, wherein the injectable resorbable bone graft material further comprises an accelerant.

25. The method of claim 24, wherein the accelerant is selected from the group consisting of calcium sulfate dihydrate, calcium sulfate dihydrate coated with sucrose, potassium sulfate, and sodium sulfate.

26. The method of claim 19, wherein the injectable resorbable bone graft material further comprises one or more additives selected from the group consisting of bone marrow aspirate, platelet concentrate, blood, antibiotics, chemotherapeutic agents, growth factors, and analgesics.

27. The method of claim 19, wherein the diluent to powder weight ratio is 0.19:1 to 0.31:1.

28. A method for treating bone defects comprising the steps of mixing a powder comprising between about 99.8 to 100 percent by weight calcium sulfate hemihydrate, the calcium sulfate hemihydrate consisting of thick, stubby, rod-like crystals having a low water carrying capacity, with a diluent to produce an injectable resorbable bone graft material in the form of a paste, wherein when undergoing dry-testing, said bone graft material has a compressive strength of approximately 88 MPa within 24 hours after said mixing step.

29. The method of claim 28, wherein said bone graft material has a compressive strength exceeding approximately 106 MPa within 24 hours after said mixing step.

30. The method of claim 28, wherein the diluent is water or a solution comprising an inorganic salt or a cationic surface active agent.

31. The method of claim 28, wherein the calcium sulfate hemihydrate is formed by immersing calcium sulfate dihydrate in a solution of water and an inorganic salt to form a mixture, and heating the mixture to substantially its boiling point at atmospheric pressure such that the calcium sulfate dihydrate is converted to calcium sulfate hemihydrate.

32. The method of claim 28, wherein the injectable resorbable bone graft material has a working time of at least 5 minutes following mixing.

33. The method of claim 28, wherein the injectable resorbable bone graft material further comprises an accelerant.

34. The method of claim 33, wherein the accelerant is selected from the group consisting of calcium sulfate dihydrate, calcium sulfate dihydrate coated with sucrose, potassium sulfate, and sodium sulfate.

35. The method of claim 28, wherein the injectable resorbable bone graft material further comprises one or more additives selected from the group consisting of bone marrow aspirate, platelet concentrate, blood, antibiotics, chemotherapeutic agents, growth factors, and analgesics.

36. The method of claim 28, wherein the diluent to powder weight ratio is 0.19:1 to 0.31:1.

* * * * *